Jan. 1, 1974 S. L. ADLER Re. 27,866

APPARATUS FOR THE AUTOMATIC DETERMINATION OF THE COAGULATION, AGGREGATION AND/OR FLUOCCULATION, OR THE LIKE, RATES OF FLUIDS, AND NOVEL REACTION INTENSIFYING AGENT FOR USE THEREWITH

Original Filed Dec. 4, 1969 2 Sheets-Sheet 1

INVENTOR
STANFORD L. ADLER
BY
ATTORNEY

APPARATUS FOR THE AUTOMATIC DETERMINATION OF THE COAGULATION, AGGREGATION AND/OR FLUOCCULATION, OR THE LIKE, RATES OF FLUIDS, AND NOVEL REACTION INTENSIFYING AGENT FOR USE THEREWITH

Original Filed Dec. 4, 1969 2 Sheets-Sheet 2

INVENTOR
STANFORD L. ADLER
BY
ATTORNEY

United States Patent Office

Re. 27,866
Reissued Jan. 1, 1974

27,866

APPARATUS FOR THE AUTOMATIC DETERMINATION OF THE COAGULATION, AGGREGATION AND/OR FLOCCULATION, OR THE LIKE, RATES OF FLUIDS, AND NOVEL REACTION INTENSIFYING AGENT FOR USE THEREWITH

Stanford L. Adler, Westchester County, N.Y., assignor to Technicon Corporation, Tarrytown, N.Y.

Original No. 3,650,698, dated Mar. 21, 1972, Ser. No. 881,971, Dec. 4, 1969. Application for reissue Dec. 14, 1972, Ser. No. 314,930
Int. Cl. B03c *1/02;* G01n *11/00, 33/16*
U.S. Cl. 23—253 R 11 Claims

Matter enclosed in heavy brackets [ ] appears in the original patent but forms no part of this reissue specification; matter printed in italics indicates the additions made by reissue.

ABSTRACT OF THE DISCLOSURE

Apparatus for the determination of the coagulation rate or the like of fluids, wherein dispensing means are operable to successively dispense blood plasma samples, in turn and at a precisely metered rate, onto spaced-apart measured quantities or spots of a dried suspension of a reaction intensifying agent carried on an advancing film strip. The intensifying agent may comprise magnetic iron oxide particles. Subsequent to incubation of the sample-intensifying agent mixture, additional dispensing means are operable to dispense a precisely metered quantity of prothrombin reagent into the film strip. The resulting sample-reagent-intensifying agent mixture is subjected to rotating magnetic fields, with the result that the moving magnetic particles promote mixing and, also, are operative to collect one or more of the fibrin strands, whereby the mixture, which is substantially turbid, undergoes a sharp change in its optical transmission properties, which change is detected by light sensitive means for the measurement of the prothrombin time of the blood plasma sample of interest.

BACKGROUND OF THE INVENTION

(1) Field of the invention

This invention relates to new and improved apparatus and reaction intensifying agent for determining the coagulation, agglutinations, and/or flocculation or the like rates of fluids and, more specifically, to such apparatus and reaction intensifying agent as are particularly adapted to the determination of the Prothrombin Time of blood plasma samples.

(2) Description of the prior art

Although a wide variety of methods and apparatus are known in the prior art for the determination of the Prothrombin Time of blood plasma samples for essential diagnostic use, it may be understood that, in general, no prior art method and/or apparatus is known which can accomplish this essential Prothrombin Time determination in fully automatic, rapid and consistently high accurate manner with minimum utilization of the expensive thromboplastin reagent required therefor.

More specifically, and considering first the plurality of substantially manual classical Prothrombin Time determination methods in the nature of the visually monitored loop or tilt method as developed by Dr. A. J. Quick, and described in detail, for example, in the informative publication "Coagulation Procedures" published by Dade Reagents Inc. of Miami, Florida, in January 1966, it is believed that the significant disadvantages thereof in the areas of undue time consumption, inaccuracy as occasioned by unclear coagulation reaction endpoint indication, technician error, incompetence, and/or general inattention, and/or unduly high use of the required, expensive thromboplastin reagent, are so well known to those skilled in this art as to require no elaboration here. On the other hand, although a wide variety of automatic or semi-automatic apparatus have been developed for Prothrombin Time determination, and are operable on such divergent bases as the detection of changes in the viscosity of the blood plasma sample-thromboplastin reagent mixture, or the creation of an electrically conductive path by the clotted materials, to indicate the end point or clotting time, these semi-automatic or automatic prior art apparatus will generally be found to be incapable of consistently and rapidly providing accurate Prothrombin Time determination results on a fully automatic basis with minimum use of the expensive thromboplastin reagent.

Probably the most widespread single source of error with regard to the operation of all of the Prothrombin Time determining methods and apparatus of the prior art is the fact that the same do not provide for sharp and dramatic change in a characteristic or property of the blood plasma sample-thromboplastin reagent mixture at the end point of the coagulation reaction which can be readily discerned and/or automatically detected to clearly indicate the precise point in time at which said end point occurs, and this disadvantage may be understood to be due in large measure to the fact that there are no known means by which said reaction can be intensified or enhanced to provide this most desirable shape and dramatic, readily discernible or automatically detectable change.

Of further disadvantage with regard to the Prothrombin Time determining methods and apparatus of the prior art is believed the fact that the above-discussed disadvantages thereof generally become even more pronounced when the same are utilized with diluted blood plasma samples, to thereby render the same generally unsatisfactory for diagnostic use in establishing controls for essential anti-coagulant dosage adjustments.

OBJECTS OF THE INVENTION

It is, accordingly, an object of this invention to provide new and improved apparatus for the rapid, automatic, and consistently accurate determination of the coagulation, aggregation or flocculation or the like rates of fluids, and which is particularly adapted to such determination of the Prothrombin Time of blood plasma samples.

Another object of this invention is the provision of apparatus as above which operate to substantially minimize the amount of the expensive thromboplastin reagent required for a blood plasma sample Prothrombin Time determination to thus materially reduce the cost of such determination.

Another object of this invention is the provision of a novel coagulation reaction intensifying or enhancing agent which provides for sharp and dramatic change in a readily discernible and/or automatically detectable characteristic of the blood plasma sample-thromboplastin reagent mixture at the end point of the coagulation reaction.

Another object of this invention is the provision of apparatus as above which are particularly adapted for operation with undiluted blood plasma samples.

A further object of this invention is the provision of apparatus as above which are fully and continuously automatic in operation and provide a readily interpretable, permanent readout of the determined blood plasma sample Prothrombin Times to thus eliminate most major sources of technician-occasioned inaccuracy.

A still further object of this invention is the provision of apparatus as above which require the use of only readily available components of proven dependability in the fabrication thereof to thus insure long periods of satisfactory, substantially maintenance-free apparatus operation.

SUMMARY OF THE INVENTION

As disclosed herein in a preferred embodiment directed toward the determination of the Prothrombin Time of a plurality of blood plasma samples, the apparatus of my invention comprise sample supply means which supply a stream consisting of successive ones of said blood plasma samples, and blood plasma sample dispensing means which are operable to successively dispense said blood plasma samples at a precisely metered rate. A novel coagulation reaction intensifying or enhancing agent which comprises opaque magnetic iron oxide particles as the essential ingredient thereof is supplied in the form of spaced, measured quantities or spots of a dried suspension of said agent as disposed on suitable carrier means which take the form of a substantially transparent film strip.

Automatically operable thromboplastin reagent dispensing means are provided and function to dispense precisely metered minimum quantities of said thromboplastin reagent upon demand. Further included are temperature controlled means to effect blood plasma sample incubation and bring the same to appropriate coagulation reaction temperature, rotating magnetic field generation means to generate a rotating magnetic field through said temperature controlled means, and light sensitive detection means to automatically detect the end point of the coagulation reaction and provide the desired Prothrombin Time determination accordingly.

In operation, said film strip is advanced to a first position on said temperature controlled means whereat a precisely measured quantity of a blood plasma sample is added to said reaction intensifying or enhancing agent to rapidly re-suspend the latter with the effect of said rotating magnetic field being to promote initial blood plasma sample-intensifying or enhancing agent mixing and render the resultant mixture substantially turbid or opaque. After the expiration of a period of time predetermined to provide for substantial blood plasma sample incubation, the film strip is advanced to said reagent dispensing means whereat a precisely metered quantity of the thromboplastin reagent is added to the substantially turbid or opaque blood plasma sample-intensifying or enhancing agent mixture to commence the coagulation reaction with the effect of said magnetic field on said magnetic iron oxide agent further promoting thorough blood plasma sample-thromboplastin reagent mixing. Therefrom, the film strip is advanced to the operation position of said light sensitive detecting means, which position generally coincides with the center of said rotating magnetic field. Thereafter, as the end point of the coagulation reaction is reached, the substantially turbid or opaque blood plasma sample-thromboplastin reagent-intensifying agent mixture will undergo a sharp and dramatic change in optical property through the collection of the rotating magnetic iron oxide particles in one or more of the fibrin strands generally centrally of the mixture to thus render the latter substantially transparent for immediate detection by said light sensitive detecting means, and attendant provision of a printed readout of the Prothrombin Time of the blood plasma sample of interest. Operation of the apparatus is continuous in the manner described until each of the blood plasma samples of said successive stream thereof has been determined.

DESCRIPTION OF THE DRAWINGS

The above and other objects and significant advantages of my invention are believed made clear by the following detailed description thereof taken in conjunction with the accompanying drawings wherein.

DETAILED DESCRIPTION OF THE INVENTION

Figure 1:
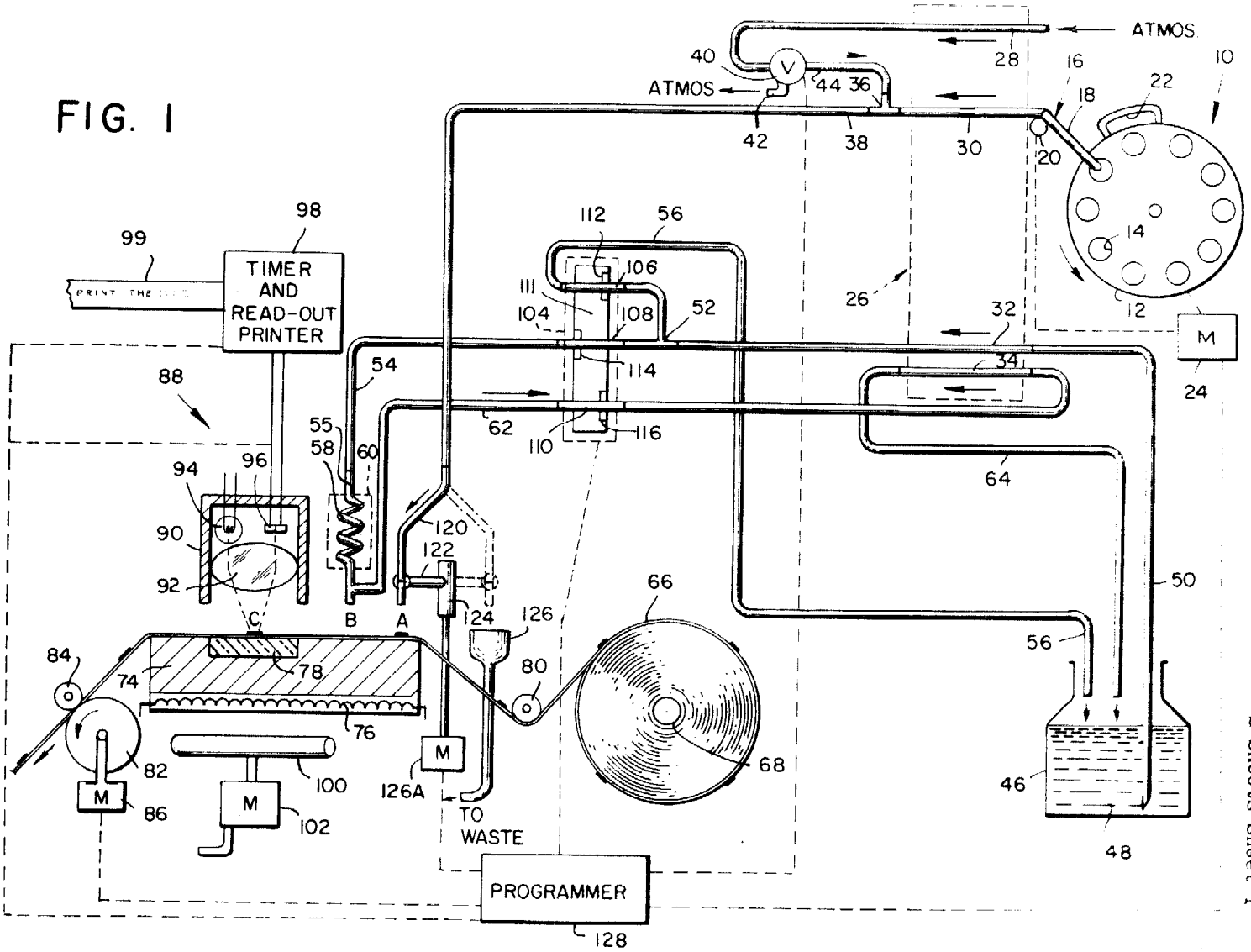
FIG. 1 is a flow diagram depicting the new and improved apparatus of my invention.

Referring now to FIG. 1, sample supply means which may, for example, take the general form of those shown and described in U.S. Pat. 3,134,263 issued May 26, 1964 to Edward B. M. De Jong, are indicated generally at 10 and comprise a turntable 12 upon which is disposed a circular array of blood plasma sample containers 14. A sample off-take device is indicated at 16 and comprises a sample off-take probe 18 and probe operating means 20, respectively. A wash liquid receptacle 22 is disposed as shown adjacent the turntable 12, while sample supply device drive means are indicated at 24 and are operative to drive each of the turntable 12 and the sample off-take probe operating means 20 in the manner described directly hereinbelow as indicated by the dashed lines extending therebetween.

In operation, the turntable 12 is intermittently rotated, or indexed, to present each of the blood plasma sample containers 14 in turn to the sample off-take probe 18, while the latter is in turn intermittently operated to immerse the inlet end of the off-take probe 18 in a thusly presented sample container for a predetermined period of time to aspirate (as described in detail hereinbelow) a predetermined measured volume of the blood plasma sample therefrom, to then transfer the said off-take probe inlet end through the ambient air for immersion in the wash liquid receptable 22 for a predetermined period of time to thus aspirate a predetermined measured volume of ambient air followed by a predetermined measured volume of said wash liquid therethrough, and to then again transfer the said off-take probe inlet end through the ambient air for immersion in the next presented sample container 14 for a predetermined period of time to thus aspirate another predetermined measured volume of ambient air therethrough and commerce the aspiration of a predetermined measured volume of the blood plasma sample from said next presented sample container.

As a result, it may be understood that a fluid stream consisting of successive, predetermined measured volumes of said blood plasma samples as spaced, in each instance, by a segment of air, a segment of the wash liquid from wash liquid receptacle 22, and a segment of air, respectively, will be supplied to the sample off-take probe 18.

A compressible tube or peristaltic proportioning pump which, for example, may take the general form of that shown and described in U.S. Pat. 3,227,091 issued Jan. 4, 1966 to Jack Isreeli et al., is indicated generally in dashed lines at 26 and, as utilized herein, may be understood to comprise a plurality of resilient, compressible pump tubes 28, 30, 32 and 34, respectively, each of which is progressively compressible or occludable by a plurality of non-illustrated pump rollers, in synchronous manner, to pump fluids therethrough in the direction from right to left as indicated by the flow directional arrows in FIG. 1.

The inlet end of compressible pump tube 30 is connected as shown to the outlet end of the blood plasma sample off-take probe 19 to provide for the aspiration of the blood plasma sample-washed liquid-air stream therethrough as discussed hereinabove. The outlet end of compressible pump tube 30 is connected as shown to one inlet of a junction conduit 36, and the outlet of the latter is connected to a blood plasma sample supply conduit 38.

The inlet end of compressible pump tube 28 is left open as shown to atmosphere, while the outlet end thereof is connected to one inlet of three-way valve means 40. One outlet conduit 42 of the three-way valve means 40 extends as indicated to atmosphere, while the other outlet conduit 44 of said three-way valve means is connected to the other inlet of the junction conduit 36. Accordingly is believed made clear that with the three-way valve means 40 in a first operating position thereof to connect compressible pump tube 28 to outlet conduit 42, air will simply be pumped through the said valve for return to atmosphere while, with said three-way valve means in a second position thereof to connect compressible pump tube 28 to valve outlet conduit 44, air will be pumped to junction conduit 36 for merger with the blood plasma sample-wash liquid-air stream being pumped therethrough from compressible pump tube 30.

A reagent container is indicated at 46 and, for use as disclosed herein in determining the end point of the blood coagulation reaction, or Prothrombin Time, of the blood plasma samples from sample supply means 10, may be understood to contain a suitable supply of thromboplastin reagent as indicated at 48. A reagent supply conduit 50 is disposed as shown within the reagent supply container 46 so that the inlet end of the former is in close proximity to the bottom of the latter for obvious purpose, and the outlet end of reagent supply conduit 50 is connected as shown to the inlet end of compressible pump tube 32, whereby is believed made clear that operation of the peristaltic pump 26 will result in the pumping of the reagent 48 from said supply container through said compressible pump tube in the indicated direction.

The outlet end of compressible pump tube 32 is connected as shown to one inlet of a junction conduit 52, while the outlet of said junction conduit is connected to a reagent dispensing conduit 54. A reagent by-pass and return conduit is indicated at 56, and the inlet end thereof is connected as shown to the other outlet of the junction conduit 52, while the outlet end of said reagent by-pass and return conduit extends as shown into the reagent supply container 46 for the return of the thromboplastin reagent thereto as described in detail hereinbelow.

Temperature control means which include a heating coil 58 connected as shown in the reagent supply conduit 54 adjacent the outlet end of the latter, and a temperature control bath as indicated in dashed lines at 60, are included to enable the precise control of the temperature of the thromboplastin reagent immediately prior to the dispensing thereof from said conduit outlet end as described in detail hereinbelow.

A suction conduit for reagent return is indicated at 62 and is connected as shown to the reagent supply conduit 54 immediately adjacent the outlet end of the later. The outlet end of the suction conduit 62 is connected as shown to the inlet end of compressible pump tube 34, while the outlet end of the latter is connected to the inlet end of a reagent return conduit 64 which extends as shown to within the reagent supply container 46 to provide for the return of the thromboplastin reagent thereto, against as described in detail hereinbelow.

Figure 2:
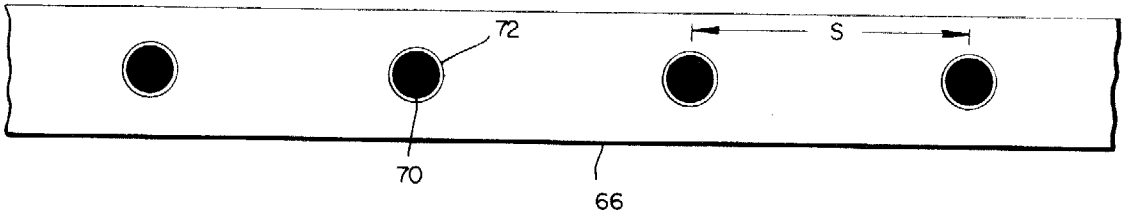
FIG. 2 is a top plan view of a portion of the film strip carrier of the apparatus of FIG. 1 illustrating the disposition of the measured quantities or spots of the reaction intensifying agent thereon.

A supply roll of a strip of a film substrate 66 which is made from any material having suitable strength, light transmission, and chemical inertness characteristics in the nature, for example, of Mylar, is disposed as shown on rotatable support means as indicated at 68. As best seen in FIG. 2, measured quantities or spots 70 of a dried suspension of a reaction intensifying or enhancing agent are disposed at substantially equally spaced intervals on the upper surface of the film strip 66. For use as disclosed herein the automatic, sequential determination of the respective Prothrombin Times of a plurality of blood plasma samples, said reaction intensifying agent may be understood to comprise substantially opaque particles of a [paramagnetic] *ferromagnetic* material such as magnetic iron oxide particles of the nature used in the manufacture of magnetic recording tape, as homogeneously suspended before drying in a suitable carrier solution. Magnetic iron oxide particles of this nature are of generally acicular configuration and have a major dimension in the range of 0.40 to 0.60 microns. Alternatively, such particles may be constituted by cobalt or nickel oxide particles.

More specifically, and for use as disclosed herein in intensifying or enhancing the blood plasma sample-thromboplastin reaction, said reaction intensifying agent may consist of a suspension of approximately 50 grams percent magnetic iron oxide particles in approximately 25 percent PVP which contains approximately 5 percent glycerine, before drying, and said suspension may be applied to film strip 66 for the formation of the spots 70 in any appropriate manner as, for example, through the use of well-known silk screening techniques. Preferably, the pH of the reagent intensifying or enhancing agent is adjusted, if necessary, to insure that the same will not react with the thromboplastin reagent upon the mixure hereof.

The paricular PVP and glycerine constituents of the magnetic iron oxide particle suspension, and the listed relative percentages of said iron oxide particles and said PVP and glycerine constituents in the reaction intensifying or enhancing agent, may be understood to be particularly effective in insuring the desired, substantially instantaneous re-suspension of said iron oxide particles in an aqueous solution upon the mixture thereof with the respective blood plasma samples as described in detail hereinbelow. It is, however, believed clear that other and different suspensions of said magnetic iron oxide particles in other and different relative percentaged with regard to said PVP and glycerine constituents, and/or with other and different suspending agents, may prove equally useful.

Boundary means in the nature of those indicated at 72 in FIG. 2 will preferably be formed on the film strip 66 in any appropriate manner as, for example, through embossing of the latter, to effect the substantial containment in the indicated area of the reaction intensifying or enhancing agent and the respective blood plasma samples upon the re-suspension of the former in the latter as described in detail hereinbelow.

Heat sink means having a substantially level, flat upper surface are indicated at 74, and heating coil means 76 are disposed as shown adjacent the lower surface of said heat sink means to provide for the substantial maintenance of the latter at a desired temperature as should be obvious. A mirror 78 is disposed as shown in the heat sink means 74 in such manner that the upper surface of said mirror is substantially flush with the upper surface of said heat sink means.

Film strip guide and drive means are provided and comprise an idler roller 80, a film strip advance drive roller 82, and a film strip pressure roller 84 cooperatively associated with the latter as shown. Accordingly, intermittent driven rotation of the film strip advance drive roller 82 in the indicated counter-clockwise direction, as through operation of a drive motor 86, may be readily understood to function to intermittently advance the film strip 66 through the unwinding of the latter from the film strip supply roll, the passage thereof beneath idler roller 80, the passage thereof over the upper surface of heat sink means 74 in close contact therewith, and the subsequent passage thereof between the film strip advance drive roller 82 and the film strip pressure roller 84, respectively.

Photosensitive detection means are indicated generally at 88 and may be seen to comprise a suitable, generally cylindrical opaque housing 90 having a focusing lens 92 disposed therein as shown. A light source is indicated at 94, and light detection means which may, for example, take the form of a photoelectric cell, are indicated at 96, and each of said light source and said photoelectric cell are positioned within the housing 90 as shown in such manner that the light beam will be focused as indicated by the focusing lens 92 for impingement upon the mirror 78 and reflection therefrom for refocusing by the focusing lens 92 for impingement upon the active surface of the photoelectric cell 96.

Reaction timer and readout printing means are indicated schematically at 98 and are operatively associated as shown with the photoelectric cell 96 to provide for reaction timing and readout printing on a tape 99 as described in detail hereinbelow.

A bar magnet of appropriate field strength is indicated at 100 and is supported as shown for rotation at appropriate rate through operation of drive motor means 102 to thereby establish a rotating magnetic field, the lines of force of which will, of course, extend through and above the heat sink means 74. Preferably, the bar magnet 100 is disposed relative to the mirror 78 in such manner that the respective centers thereof are in substantial vertical alignment as seen in FIG. 1, whereby it may be understood that the center of the rotating magnetic field established by rotation of the bar magnet 100 will be generally coincident with the center of the mirror 78.

Multi-element snap-action valve means are indicated generally in dashed lines at 104 and may, for example, take the general form of those shown and described in the co-pending application for United States Patent of Carl V. Johnson et al., entitled "New and Improved Method and Apparatus for Simultaneously Controlling the Flow of Fluids in a Plurality of Flow Paths," Ser. No. 864,262, filed Sept. 22, 1969 and assigned to the assignee hereof. Each of the reagent by-pass and return conduit 56, the reagent dispensing conduit 54, and the suction conduit 62 pass as shown through the valve means 104 for control by the latter of the respective fluid flows therethrough and, to this effect, it may be understood that at least the portion of each of said conduits which passes through said valve means is constituted by a compressible tube or conduit as indicated respectively at 106, 108 and 110.

The valve means 104 comprise a valve actuator member 111 having projection bar members 112, 114, and 116 formed thereon with said bar members being respectively operatively associated with the compressible conduit portion 106, 108 and 110. In operation for use as disclosed in detail hereinbelow, it may be understood that the valve means 104 are arranged so that the valve actuator 111 is pivotally moveable, in extremely rapid, snap-action manner between a first position thereof wherein the bar member 114 contacts and substantially compresses or occludes compressible conduit portion 108 against a non-illustrated platen to substantially prevent fluid flow therethrough, while neither of bar members 112 or 116 contacts compressible conduit portions 106 and 110 and thus does not interfere with the respective flow of fluids therethrough, to a second position of said valve actuator wherein bar members 112 and 116 respectively contact and substantially compress or occlude compressible conduit portions 106 and 110 against said platen to substantially prevent fluid flow therethrough, while bar member 114 does not contact compressible tube portion 108 and thus does not interfere with the flow of fluids therethrough. Accordingly, it is believed made clear that with said valve actuator 111 in said first position thereof, fluid flow through reagent dispensing conduit 54 will be substantially prevented, while fluid flow through the respective reagent by-pass and return conduits 56 and suction conduit 64 will be unaffected. Conversely, with said valve actuator 111 in said second position thereof, it is believed clear that fluid flow through the respective reagent by-pass and return conduit 56 and suction conduit 64 will be substantially prevented, while fluid flow through reagent dispensing conduit 54 will be unaffected.

A blood plasma sample dispensing probe is indicated at 120 and the inlet end thereof is connected as shown to the outlet end of blood sample supply conduit 38. The blood sample dispensing probe 120 is supported as shown adjacent the outlet end thereof from the arm 122 of blood sample dispensing probe operating means 124. The blood sample probe operating means 124 are operated from drive motor means as indicated at 126A for oscillatory movement to move the inlet end of the blood sample dispensing probe 120 in an arc between the depicted first position thereof wherein said outlet end is in substantial vertical alignment with a measured quantity or spot 70 of the reagent intensifying or enhancing agent on the upper surface of film strip 66 when the latter is in a specific position thereof as described in detail hereinbelow, and a second position of the probe as depicted in phantom in FIG. 1 wherein said dispensing probe outlet end is in general vertical alignment with a blood plasma sample and wash liquid collection receptacle 126A which leads as indicated to waste.

Programmer means which may take any appropriate form in the nature, for example, of cam-operated electrical programmer means are indicated schematically at 128 and are operatively connected as indicated by the dashed lines to each of the sample supply means drive motor 24, the three-way valve means 40, the multi-element valve means 104, the blood plasma sample dispensing probe operating means drive motor 126, the film strip advance drive roller drive motor 86, the photoelectric cell 96, and the timer and readout printing means 98, respectively.

OPERATION

For typical use in the automatic, sequential determination of the respective Prothrombin Times of a plurality of blood plasma samples, it may be understood that each of the blood plasma sample containers 14 would contain an undiluted blood plasma sample from a different patient, each of which will have been previously treated in classical manner with a fixative reagent in the nature of sodium oxalate or sodium citrate immediately upon withdrawal from the patient, and will preferably be maintained at approximately 4° to 5° C., in the relevant blood plasma sample container 14 to inhibit clotting factor deterioration through the use of non-illustrated cooling means which may be included in or operatively associated with the sample supply device 10.

The three-way valve means 40 would be arranged to operate, under the control of programmer 128, to be in the second position thereof to introduce air to the blood plasma sample-wash liquid-air stream flowing through junction conduit 36 only when the wash liquid segments are flowing therethrough to thus air segment each of said wash liquid segments to materially improve the cleansing action thereof, while insuring the flow of each of the aspirated blood plasma samples as a continuous stream to the blood plasma sample dispensing probe 120. The reagent supply container 46 would, of course, contain a supply of the thromoplastin reagent 48 sufficient for the Prothrombin Time determination of each of the blood plasma samples carried from the sample supply means 10.

In addition, the film strip advance drive roller motor 86 would be arranged to operate the film strip advance drive roller 82, under the control of programmer 128, to alternatively, intermittently advance the film strip 66 to two positions thereof relative to the focal point of lens 92, the outlet end of reagent dispensing conduit 54, and the outlet end of the blood plasma sample dispensing probe 120, respecstively, and to enable the dwelling of said film strip in each of said positions for different predetermined periods of time as described in detail hereinbelow. More specifically, it may be understood that said film strip advance drive roller would initially be operated to advance the film strip to the position thereof depicted in FIG. 1 wherein a leading measured quantity or spot 70 of the reaction intensifying or enhancing agent (as now thoroughly mixed and re-suspended with a blood plasma sample and a precisely metered amount of the thromboplastin reagent in the manner described in detail hereinbelow) would be disposed as indicated at position C on the mirror 78 at the exact focal point of the focusing lens 92, while the next succeeding or trailing measured quantity or spot 70 of said reaction intensifying or enhancing agent would be disposed as indicated at position A directly below the outlet end of blood plasma sample dispensing probe 120 when the same is in the depicted blood plasma sample dispensing position thereof as shown in FIG. 1. Accordingly it is believed made clear that the spacing S (FIG. 2) between said measured quantities or spots 70 of the reaction intensifying or enhancing agent on the upper surface of the film strip 66 is predetermined to substantially coincide with the distance between said lens focal point on mirror 78 and the point on heat sink 74 which is in substantial vertical alignment with the outlet end of the blood plasma sample dispensing probe 120. In said second position to which the film strip 66 is intermittently advanced by operation of said film strip advance drive roller 82, it may be understood that the former would be positioned so that the measured quantity or spot 70 of the reaction intensifying or enhancing agent which had been disposed at position A would now be advanced for disposition in substantial vertical alignment with the outlet end of reagent dispensing conduit 54 at position B as indicated in FIG. 1, it being believed clear that with the film strip 66 thusly disposed, no measured quantities or spots 70 of the reaction intensifying or enhancing agent will be disposed at either of positions A or C.

The multi-element valve means 104 would be arranged to operate, again under the control of programmer 128, to be in said second position thereof to enable reagent flow from reagent supply conduit 32 through compressible conduit portion 108 to reagent dispensing conduit 54 only for a period of time predetermined to substantially coincide with the period of time in which the film strip 66 is dwelled in a said second position thereof to position a measured quantity or spot 70 of the reaction intensifying or enhancing agent in substantial vertical alignment with the outlet end of said reagent dispensing conduit. At all other times, it may be understood that the multi-element valve means 104 would be arranged to be in said first position thereof to permit fluid flow only through compressible conduit portions 106 and 110. With further regard to the reagent dispensing conduit 54, it may be understood that temperature control bath 60 would be arranged to maintain the temperature of the temperature control coil 58 at approximately 37° C. to thus insure the dispensing of the thromboplastin reagent at substantially this temperature.

The blood plasma sample dispensing probe operating means 124 would be arranged to operate, through drive motor 126A under the control of programmer 128, to position the blood plasma sample dispensing probe 120 as depicted in the blood plasma sample dispensing position thereof only for a part of the time when the film strip 66 is dwelled in a said first position thereof with a measured quantity or spots 70 of the reagent intensifying or enhancing agent being disposed as depicted in FIG. 1 at position A, and to at all other times position said blood-plasma sample dispensing probe in the position depicted in phantom in FIG. 1 whereby the remainder of each of the blood plasma samples that is not dispensed for test, and the respective inter-sample wash liquid segments, will be dispensed into receptacle 126 for flow therefrom to waste.

Finally, heating coil means 76 would be arranged to operate to maintain the temperature of the heat sink means 74 at approximately 37° C.

In operation, and assuming steady state operational conditions to have been reached and the film strip 66 to have just been advanced to a first position thereof to dispose succeeding measured quantities or spots 70 of the reagent intensifying or enhancing agent at positions A and C as depicted in FIG. 1, it may be understood that the blood plasma sample dispensing probe 120 will just have been moved to the depicted position thereof and that a blood plasma sample will just be commencing to flow therefrom as a continuous stream to fall upon and mix with the measured quantity or spot 70 of the reaction intensifying or enhancing agent now disposed at position A with resultant almost instantaneous re-suspension of the magnetic iron oxide particles therein. This almost instantaneous resuspension, and concomitant commencement of the thorough mixing of said iron particles in said blood plasma sample will be significantly enhanced by the effect of the rotating magnetic field generated by the rotation of the bar maget 100 upon said magnetic iron oxide particles as should be obvious.

After the expiration of a time period predetermined to enable the dispensing of the desired amount of the blood plasma sample, which time period may, for example, be of approximately 1.5 to 2 seconds duration, it may be understood that the blood plasma sample dispensing probe operating means will be actuated to move said probe to said second position thereof directly over wash-liquid collection receptacle 126 to enable the flow of the remainder of the blood plasma sample, and the succeeding air segment, air segmented wash liquid segments, and air segments, through said blood plasma sample dispensing probe to insure a thorough cleansing of the latter and prevent the contamination of the succeeding blood plasma sample by the residue of the just dispensed blood plasma sample, to obvious advantage.

Preferably, the film strip advance drive roller 82 will, at this point, be maintained stationary for approximately 55 seconds to dwell the film strip 66 in this first position thereof for that period of time to bring the thusly dispensed blood plasma sample and the measured quantity or spot 70 of the reaction intensifying or enhancing agent up to the preferred test temperature of approximately 37° C. and commence the require incubation of said blood plasma sample.

At the expiration of this dwell period, it may be understood that the film strip advanced drive roller 82 will be operated to advance the film strip 66 to said second position thereof wherein the now thoroughly mixed blood plasma sample and reagent intensifying or enhancing agent measured quantity 70 will be disposed at position B directly beneath the outlet end of reagent dispensing conduit 54. Concomitantly, the multielement valve means 104 will be rapidly shifted to the second position thereof to enable the commencement of reagent dispersing, in precisely metered amount, through the reagent dispensing conduit 54 at approximately 37° C. As the thusly dispense reagent joins the blood plasma sample and the new re-suspended magnetic iron oxide particles to commence the desired blood plasma sample-thromboplastin reagent reaction, it may be understood that the advantageous thorough mixture thereof will continue to be enhanced by the action of the rotating magnetic field on said magnetic iron oxide particles. With a dwell period of approximately 2 seconds for the film strip 66 in this second position thereof, it may be understood that a reagent dispensing time ranging from approximately 1½ to 2 seconds may be utilized. Too, for purposes of determining the Prothrombin Time of the blood plasma sample of interest, it may be understood that the time of shifting of the multi-element valve means to said second position thereof may be taken as time 0 and communicated from the programmer 128 to the timer and readout printing the means 98 since this time substantially coincides with the time the thromboplastin reagent first contacts said blood plasma sample to commence the coagulation reaction.

At the expiration of the period of time predetermined to be sufficient to enable the precise dispensing of the desired quantity of the thromboplastin reagent through reagent dispensing conduit 54, it may be understood that multi-element valve means 104 will be rapidly shifted to return to said first position thereof wherein further reagent flow from reagent supply conduit 32 to reagent dispensing conduit 54 will be prevented by the abrupt closure of compressible conduit portion 108, and the supply of reagent being pumped through compressible pump tube 32 by-passed instead through reagent by-pass and return conduit 56 for return to reagent supply container 46. This shifting of the multi-element valve means to said second position thereof will, in addition, be effective to open compressible conduit portion 110 with attendant creation of considerable suction in suction line 62 through the operation of compressible pump 34 to thus insure that any thromboplastin reagent remaining in the outlet end portion of the reagent dispensing conduit 54 after the completion of reagent dispensing is sucked therefrom through the section 62 for return to reagent supply container 46 on reagent return conduit 64 to thus further insure the precise dispensing of exactly the desired amount, only, of said reagent and substantially prevent any waste of the latter to obviously significant advantage.

At the expiration of this approximately 2 seconds dwell period, the film strip advance drive roller 82 is operated to again advance the film strip 66 to a said first position thereof wherein the blood plasma sample-reagent-reagent intensifying or enhancing agent mixture under discussion will be advanced to position C which, as discussed hereinabove, substantially coincides with the focal point of focusing lens 92 on mirror 78. Although appropriate spacing between the respective measured quantities or spots 70 of the reaction intensifying or enhancing agent on the film strip 66 relative to the spacing between said focusing lens focal point and the outlet end of blood plasma sample dispensing probe 120 when the latter is in the dispensing position thereof may be utilized to insure that the mixture of interest comes to rest precisely at position C, it may be understood that a further input from the photoelectric cell 96 to the programmer 128 may, in addition, be utilized to insure this occurs. More specifically, it may be understood that since this blood plasma sample-reagent-reaction intensifying agent mixture is at this point still substantially opaque or turbid due to the wide distribution of the substantially opaque magnetic iron oxide particles therein, the movement of the said mixture into position C will function to break the beam of light from light source 94 to said photoelectric cell, and that this occurrence may be utilized for the provision of a control signal to programmer 128 to immediately discontinue operation of the film strip advance drive roller drive motor 86 as should be obvious.

Figure 3:
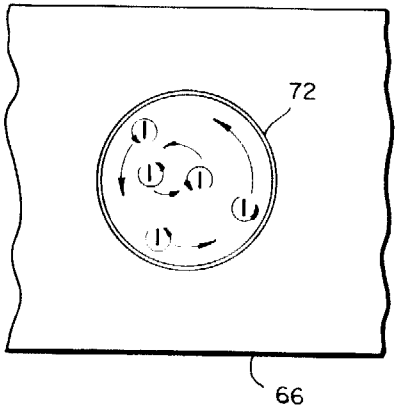
FIG. 3 is a top plan view of a portion of the film strip carrier of FIG. 2 illustrating the manner in which the reaction intensifying agent promotes blood plasma sample-thromoboplastin mixing.

As the blood plasma sample-reagent-reaction intensifying agent mixture of interest assumes position C, it may be understood that the very thorough mixing thereof through movement of the magnetic iron oxide particles under the influence of the magnetic field generated by the rotating bar magnet 100 will now be very significantly enhanced. More specifically, and referring now to FIG. 3 wherein a number of the acicular magnetic particles are depicted to better illustrate the thoroughness of this mixing, it may be understood that each of said particles will be caused by the action of said magnetic field to both rotate about its own axis and to rotate about the center of the mixture, as indicated in each instance by the rotational direction arrows, to significantly promote the desired blood plasma sample-thromboplastin reaction as should be obvious.

As the coagulation reaction proceeds it may be understood that polymerization of the fibrinogin in the blood sample into fibrin strands will result, and that these fibrin strands will be in essence collected by the multitude of rotating magnetic iron oxide particles which will be continually rotated therethrough. As this fibrin strand collection continues to occur, strand collection continues to occur, the said fibrin strands will become interwoven until such time as the same are in essence collected by the magnetic iron oxide particles into one or more relatively large globules or agglomerates thereof to indicate that the reaction end point or blood plasma sample clotting time has been reached.

Figure 4:
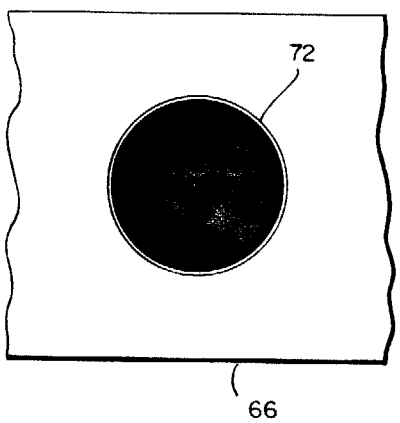
FIGS. 4 and 5 illustrate the sharp and dramatic change in the turbidity of the blood plasma sample-reagent-reaction intensifying agent mixture attendant the completion of the coagulation reaction.
Figure 5:
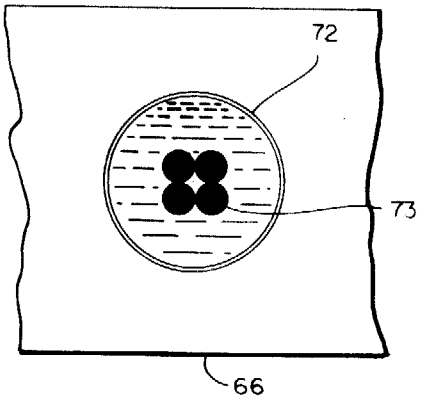

More specifically, and referring now to FIGS. 4 and 5, it may be understood that FIG. 4 depicts the blood plasma sample-reagent-reaction intensifying agent mixture as the same initially assumes position C and clearly illustrates that the said mixture is, at this point, substantially turbid or opaque due to the substantially even distribution of the multitude of magnetic iron oxide particles therein. However, as the coagulation reaction progresses to the end point or clotting time thereof, as discussed directly hereinabove, it may be understood that the interaction between the fibrin strands and said magnetic iron oxide particles, and collection thereof in one or more relatively large globules as indicated at 73 in FIG. 5 will result in a rapid and dramatic change in the optical characteristics of the said mixture to those depicted in FIG. 5, wherein the said fibrin-magnetic iron oxide particle globules will be collected generally centrally of said mixture to result in sharp and dramatic change in the light transmission properties thereof from the substantially turbid or opaque to the substantially translucent or transparent.

This sharp and dramatic change in the turbidity or opaqueness of the mixture will, of course, be immediately detected by the photoelectric cell 96 through the sharp and dramatic reopening of the light path thereto for the beam of light from light source 94, as should be obvious, with resultant instantaneous provision thereby of an appropriate signal to the timer and readout printing means 98 to stop said timer (it being recalled that said timer was started at time 0 by the shifting of multi-element valve means 104 into said second position thereof to commence thromboplastin reagent dispensing) and provide a printed readout in seconds upon the tape 99 of the Prothrombin Time of the blood plasma sample of interest, to be followed by appropriate resetting of the timer and readout printing means 98 in preparation for the determination of the Prothrombin Time of the succeeding blood plasma-sample.

Concomitantly with the movement of the blood plasma sample-reagent-reaction intensifying agent mixture under discussion into position C, it is believed clear that the succeeding measured quantity or spot 70 of the reaction intensifying or enhancing agent or film strip 66 will, of course, have been moved into position A for addition of the succeeding blood plasma sample thereto through blood plasma sample dispensing probe 120, and commencement of the approximately 55 second incubation period of said succeeding blood plasma sample Operation of the apparatus of my invention is, of course, automatically continuous as described until the Prothrombin Time for each of the blood plasma samples supplied from sample supply device 10 has been determined. For a typical application of this nature, 60 of said blood plasma samples may be positioned at one time on the sample supply means turntable 12, and approximately only one hour will be required for the determination of the Prothrombin Times of all of said blood plasma samples.

Of particular advantage with regard to the new and improved, automatic coagulometer apparatus of my invention is believed the fact that, as applied to the determination of the respective Prothrombin Times of a plurality of blood plasma samples, the same provides for absolute minimization in the amount required of the expensive thromboplastin reagents. More specifically, it is believed clear that, through the use of the proportioning pump 26, the rapidly acting multi-element valve means 104, the reagent dispensing conduit 54, the reagent by-pass and return conduit 56, and the suction conduit 62, the precisely metered dispensing of only that quantity of the thromboplastin reagent which is required for the test purposes is insured, and that waste of said reagent is subtsantially prevented. Thus, for example, the apparatus of my invention may be understood to make possible the precise and automatic determination of the Prothrombin Time of an undiluted blood plasma sample in a ratio of approximately 0.02 ml. of thromboplastin reagent to each 0.01 ml. of blood plasma sample as opposed, for example, to blood plasma sample Prothrombin Time determination made in accordance with the principles of the prior art which require approximately 0.2 ml. of thromboplastin reagent per 0.1 ml. of blood plasma sample. Thus may be readily appreciated that the apparatus of my invention make possible a very substantial and significant reduction of approximately 90 percent in the amount of expensive thromboplastin reagent required per blood plasma sample Prothrombin Time determination.

The significant advantages attendant the fully automatic and extremely accurate operation of the apparatus of my invention with regard to the elimination of technician errors and the like are believed so clear as to not require further elaboration here.

Although disclosed hereinabove in the form of a preferred embodiment which is directed toward the automatic, successive determination of the respective Prothrombin Times of a plurality of blood plasma samples, it is believed clear that the apparatus of my invention would have significant utilization for different purposes. More specifically, it is believed clear that through suitable modification the said apparatus could readily be adapted to the determination, for example, of the partial thromboplastin time, or PTT, of the blood plasma samples to enable the use thereof for the more specific isolation of the factor or factors causing deficiencies in the clotting time of a patient's blood. In addition, and again with suitable modification, it is believed clear that the apparatus of my invention may be utilized in the determination of the end point of a polymerization type reaction, the end point of which is evidenced by an abrupt change in viscosity, in a wide variety of liquids other and different than blood plasma samples. Thus, for example, the apparatus of the invention could be utilized to determine the end point of flocculation reaction as would occur in pregnancy testing and/or the end point of the agglutination reaction as would occur in testing for rheumatoid arthritis.

Too, although disclosed herein by way of example for the determination of the Prothrombin Times of undiluted blood plasma samples, it may be understood that the apparatus of the invention is applicable for such determination in reliable and accurate manner for blood plasma samples diluted down as far as 5 percent to thus enable the use of the apparatus to establish anti-coagulant dosage controls for essential therapeutic use.

While I have shown and described the preferred embodiment of my invention, it will be understood that the invention may be embodied otherwise than as herein specifically illustrated or described, as that certain changes in the form and arrangement of parts and in the specific manner of practicing the invention may be made without departing from the underlying idea or principles of this invention within the scope of the appended claims.

What is claimed is:

1. [In] *An* apparatus for determining the coagulation rates or the like of fluids through the measurement of the reaction time thereof with a coagulation reagent or the like, means to mix a said fluid and said reagent with a reaction intensifying agent which, upon activation, will intensify said reaction and provide a readily detectable change in an optical property of said fluid-reagent-reaction intensifying agent mixture at the completion of said reaction, said reaction intensifying agent comprising a plurality of [paramagnetic] *ferromagnetic* particles, means to activate said reaction intensifying agent by subjecting said mixture to a moving magnetic field, so as to effect relative movement between said particles and said mixture, and means to monitor said optical property and to detect said optical property change to thus effect the measurement of said reaction time.

2. Apparatus as in claim 1 wherein, said reaction intensifying agent particles are of a material which is substantially chemically inert with regard to said fluid and said reagent, whereby said reaction intensifying agent will not interfere chemically with said reaction.

3. Apparatus as in claim 1 wherein, said activating means are operable to generate a rotating magnetic field, whereby said reaction intensifying agent particles will be rotated through said mixture under the influence thereof.

4. Apparatus as in claim 3 wherein, said reaction intensifying agent is substantially opaque and generally uniformly distributed throughout said fluid-reagent-reaction intensifying agent mixture at the commencement of said reaction to render the same substantially turbid, and said reaction intensifying agent is operable to collect generally centrally of said fluid-reagent-reaction intensifying agent mixture under the influence of said activating means only at the completion of said reaction with concomitant change in the turbidity of said fluid-reagent-reaction intensifying agent mixture.

5. Apparatus as in claim 4 wherein, said means to mix a said fluid and said reagent with said reaction intensifying agent comprise, means to successively supply predetermined quantities of said reaction intensifying agent, means to successively mix a predetermined quantity of a said fluid with each of said reaction intensifying agent quantities, and means to successively mix a predetermined minimum quantity of said reagent with each of said reaction intensifying agent-fluid quantity mixtures to effect said reaction.

6. Apparatus as in claim 5 wherein, said means to successively supply said predetermined quantities of said reaction intensifying agent comprise, strip-like carrier means having said quantities disposed thereon in substantially equally spaced manner.

7. Apparatus as in claim 6 wherein, said carrier means are substantially transparent, and said detecting means comprise light sensitive means which are operable to direct a beam of light through said mixture and through said carrier means to thereby detect said change in the turbidity of said fluid-reagent-reaction intensifying agent mixture through the detection of the attendant change in the light transmission characteristics thereof.

8. Apparatus as in claim 6 wherein, said magnetic field generation means are disposed remotely of said carrier means and said mixtures.

9. Apparatus as in claim 1 wherein, said means to mix a said fluid and said reagent with said reaction intensifying agent comprise, means to successively supply predetermined quantities of said reaction intensifying agent, means to successively mix a predetermined quantity of a said fluid with each of said reaction intensifying agent quantities, and means to successively mix a predetermined minimum quantity of said reagent with each of said reaction intensifying agent-fluid quantity mixtures to effect said reaction.

10. Apparatus as in claim 9 wherein, said means to successively supply said predetermined quantities of said means reaction intensifying agent comprise, strip-like carrier means having said quantities disposed thereon in substantially equally spaced manner.

11. Apparatus as in claim 10 wherein, said carrier means are substantially transparent.

References Cited

The following references, cited by the Examiner, are of record in the patented file of this patent or the original patent.

UNITED STATES PATENTS

| | | | |
|---|---|---|---|
| 2,113,063 | 4/1938 | Stryker et al. | 23—253 TP UX |
| 2,678,729 | 5/1954 | Spodig | 210—222 |
| 3,146,163 | 8/1964 | Brewer | 23—253 X |
| 3,395,210 | 7/1968 | Lenahan et al. | 23—230 B X |
| 3,470,067 | 9/1969 | Warren et al. | 210—222 X |
| 3,492,096 | 1/1970 | Hattersley | 23—230 B |

OTHER REFERENCES

Hyland, Clotek System Instruction Manual, D-219/35-0055 B, 4 pages (October 1968).

JOSEPH SCOVRONEK, Primary Examiner

U.S. Cl. X.R.

23—183, 200, 230 B, 230 A, 253 TP, 259; 73—64.1; 210—42, 222; 260—695; 356—39, 208